United States Patent
Marsh

(10) Patent No.: US 8,133,202 B2
(45) Date of Patent: Mar. 13, 2012

(54) DISPOSABLE NEEDLE AND HUB ASSEMBLY

(75) Inventor: Ronald W. Marsh, Hackettstown, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 791 days.

(21) Appl. No.: 11/546,216

(22) Filed: Oct. 11, 2006

(65) Prior Publication Data

US 2007/0149924 A1    Jun. 28, 2007

Related U.S. Application Data

(60) Provisional application No. 60/725,637, filed on Oct. 13, 2005.

(51) Int. Cl.
*A61M 5/00* (2006.01)
(52) U.S. Cl. ...................................................... 604/117
(58) Field of Classification Search ............ 604/117
See application file for complete search history.

(56) References Cited

U.S. PATENT DOCUMENTS

| | | | | |
|---|---|---|---|---|
| 5,941,857 A | * | 8/1999 | Nguyen et al. | 604/263 |
| 5,944,700 A | * | 8/1999 | Nguyen et al. | 604/263 |
| 5,997,509 A | * | 12/1999 | Rosengart et al. | 604/164.01 |
| 6,146,361 A | | 11/2000 | DiBiasi et al. | |
| 6,200,296 B1 | | 3/2001 | DiBiasi et al. | |
| 6,517,516 B1 | * | 2/2003 | Caizza | 604/110 |
| 6,544,238 B1 | | 4/2003 | Smedegaard et al. | |
| 6,843,783 B2 | | 1/2005 | Ooyauchi | |
| 2008/0045900 A1 | * | 2/2008 | Alchas et al. | 604/117 |

FOREIGN PATENT DOCUMENTS

| | | |
|---|---|---|
| EP | 1 449 555 B1 | 6/2006 |
| JP | 2001-333981 | 12/2001 |
| JP | 2005-527249 | 9/2005 |
| JP | 2007-502156 | 2/2007 |

* cited by examiner

*Primary Examiner* — Nicholas Lucchesi
*Assistant Examiner* — Pritesh Patel
(74) *Attorney, Agent, or Firm* — Roylance, Abrams, Berdo and Goodman, LLP

(57) ABSTRACT

A needle assembly including a cover, an inner shield, a needle and a hub assembly is provided. After use, the cover is placed over the distal (patient) end of the needle and the inner shield can be used to cover the proximal (non-patient) end of the needle. The inner shield comprises flexible extensions above its open end to secure the inner shield over the proximal end of a needle in the needle assembly. A needle hub is also provided that eliminates adhesive bumps at the base of the needle and further distributes needle angular bending along an irregular surface, which facilitates proper insertion technique and effective needle length. The hub further includes stanchions or castellations on its edge such that when the patient uses proper injection techniques, the edges of the hub leave a distinctive impression in the skin of a user for a short period of time.

20 Claims, 20 Drawing Sheets

DISPOSABLE NEEDLE AND HUB ASSEMBLY

This Application is claiming the benefit under 35 U.S.C. 119(e) to Provisional Application Ser. No. 60/725,637, filed Oct. 13, 2005.

FIELD OF THE INVENTION

The present invention relates generally to a disposable injection needle and hub assembly, particularly one in which the hub provides an effective usable needle length and a non-patient needle end shield. These features allow a user to administer medication into a tissue layer at a predetermined depth, and to dispose of the device without fear of injury due to the exposed needle tip.

BACKGROUND OF THE INVENTION

Insulin injections are traditionally given with either an insulin syringe, usually having an integrated needle permanently or semi-permanently incorporated, or an insulin pen whereby a disposable pen needle is attached to facilitate drug container access and allow fluid egress from the container through the needle into the patient. As technology and competition advance, driving the desire for shorter, thinner, less painful, and more efficacious insulin injections, the design of the needle hub becomes more and more important. Hub designs need to proactively address ergonomically improving injection technique, injection depth control and accuracy, the ability to be safely used and transported to disposal, and protection against misuse while maintaining the ability to be economically manufactured on a mass production scale.

In order to achieve the desired injection depths for shallow subcutaneous and intradermal injections, conventional needle hub assemblies may have a depth-limiting attachment to achieve the desired injection depth, which requires the needle to be longer in length and less structurally resilient to non-perpendicular insertion caused by improper injection technique and general misuse overall.

Needle hub assemblies are typically molded from plastic with a center hole for allowing a needle to pass through the center. The needle is then specially made to the proper injection length on the patient side of the hub for the targeted tissue depth, as well as to have enough length on the proximal or non-patient (NP) side to interface with a medication cartridge. Epoxy or adhesive is then used to secure the needle at the proper length within the center hole. The center hole may be slightly enlarged to form a well for the adhesive to collect and to establish a bond between the needle hub assembly and the needle. FIG. 1 shows a needle hub assembly 1 that includes a cover 10, a needle cannula 31, a needle hub 30, and an inner shield 20. The needle hub 30 also includes a conventional center protrusion 40, an adhesive well 43, and an epoxy or adhesive bump 45 that surrounds the needle cannula 31.

Typically, the adhesive well 43 is overfilled causing the adhesive bump 45 to extend upward from the distal end of the needle hub along the exterior of the needle cannula 31 for a certain length or height. The height of the adhesive bump 45 from one needle assembly to the next is not uniform, but the bumps generally fall within a predetermined maximum tolerance unsuitable for shallow drug delivery. Even within this tolerance the bump reduces the overall effective needle length, to varying extents from needle-to-needle, which can significantly affect depth of medication delivery. Specifically for needles designed with short effective lengths aimed at shallow delivery below the skin, this could affect whether the medication will be delivered to the intradermal tissue layer or the shallow subcutaneous tissue layer.

Other lengths however, can be used. In any case, it is important to provide a hub design which enables tightly-controlled tolerances of needle length (usable) in order to achieve accurate drug delivery specifically targeted to a desired depth. In specific embodiments the delivery is in either the intradermal or shallow subcutaneous tissue.

Other negative effects of the adhesive bump include potential bruising to the patient when administered an injection and producing a single lateral stress point at the needle/bump junction which can cause the needle cannula 31 to more easily bend when used improperly. The bruising caused by the adhesive bump 45 can be caused by the shape of the bump and the force placed on the pen injection device to insure that the needle cannula is fully inserted, and that the injection depth is correct. The effective needle length is important in that as manufacturers attempt to reduce the discomfort associated with injections by manufacturing smaller diameter needles with shorter tightly controlled lengths, the tissue layer in which the medication is injected can vary and the physiologic response becomes more critical. It is important that the injection device be capable of delivering the medication to the targeted tissue layer. Therefore, the effective length of the needle and its associated tolerance is critical in meeting the requirements of the medication dosage and expectations of the user. The user immediately after administering injection may not notice that the medication missed the targeted tissue layer until there is some adverse physical reaction.

Another feature of the needle hub assembly 1 in FIG. 1 is a shield 20 for the proximal or NP end needle point that is exposed when the used needle hub assembly is to be disposed. After the injection has been administered, the needle hub assembly 1 is removed from the medication cartridge (not shown) and prepared for disposal in a biological sharps container or the like. However, at times when a biological sharps disposal container is not available, a user may decide to wait until such a container is available. In the diabetic community, for instance, many times insulin injectors who must give themselves injections while away from home do so with their pen and pen needle and afterward, transport their pen needles home for disposal per their standard, appropriate, sharps disposal means. Typically, if a container for disposal of sharp biological instruments is not available, users of the injection device improperly place the used needle hub assembly in a pocket or purse for proper disposal at a later time, which may result in inadvertent needle sticks during storage, transportation, or disposal of the needle hub. Although the proximal or NP end of the needle 33 does not protrude beyond the outer diameter of the proximal end of the needle hub assembly 30, there is a chance that a person may be pricked by the NP-end 33 of the needle 31 while trying to remove the needle hub assembly 30 from a pocket or purse. Accordingly, the needle hub assembly 1 is fitted with a shield 20 for the NP-end 33 of the needle 31 that requires a snap-fit 35 of the cover 20 over the NP-end needle 33. The snap-fit 35 secures the flange 23 in place. The flange 23 is substantially 90 degrees and is tightly held by the snap-fit 35. The snap-fit 35 is difficult to manufacture and raises the overall manufacturing costs of the device.

An example of an NP-end needle shield is described in commonly-assigned U.S. Pat. No. 5,941,857 to Nguyen et al., the entire disclosure of which is incorporated herein by reference.

Accordingly, a need exists for a disposable injection needle and hub assembly in which the hub provides an effective usable needle length and a non-patient needle end shield.

SUMMARY OF THE INVENTION

Aspects of the present invention comprise a one-piece molded depth-limiting hub design that has a shieldable proximal or NP end with a skin seating contact plane, which enables precise usable length of the needle.

In accordance with an aspect of the present invention, a hub inner ring with stanchions provides an adhesive run-off feature as well as a visual positive-reinforcement training aid according to an embodiment of the present invention.

In accordance with another aspect of the present invention, a hub having a deepened well resulting in a submerged adhesive is provided according to an embodiment of the present invention.

The design of the needle hub assembly according to an embodiment of the present invention ergonomically suggests a proper insertion technique that is substantially perpendicular to the skin to fully seat the needle into skin, which facilitates delivering the injection accurately to the desired depth.

The center hub protrusion used in embodiments of the present invention provides protection and forgiveness from cannula buckling or fracture when misused or used in accordance with poor technique. In addition, the center hub protrusion used in embodiments of the present invention facilitates stress concentration relocation, thereby sharing cannula angular bending along an irregular surface and preventing a lateral stress of 90 degrees or more.

In yet other embodiments of the present invention, a deepened well also provides protection and forgiveness from cannula buckling or fracture when misused or used in accordance with poor technique. The needle protrusion from the deepened well used in embodiments of the present invention facilitates stress concentration relocation, thereby sharing cannula angular bending along an irregular surface and preventing a lateral stress of 90 degrees or more.

Another advantage of embodiments of the present invention is that during the removal of the needle after injection, the contact plane of the needle hub assembly provides a fulcrum action at the outer ring or shroud that allows only a finite amount of the cannula to bend before proactively reducing further damage by serving to pry or withdraw the cannula from the tissue.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

It should be understood that the same reference numbers refer to the same features, elements and structures throughout the drawing figures.

DETAILED DESCRIPTION OF THE EXEMPLARY EMBODIMENT

The following description and details of exemplary embodiments of the present invention, while generally disclosed in a typical pen needle hub configuration, could more broadly apply to a needle and hub assembly for use in conjunction with, or incorporated onto, other injection devices such as syringes and infusion devices. In the case of a disposable pen needle application, the user would generally handle embodiments of the invention in the same manner as a typical commercially available pen needle.

Figure 2:
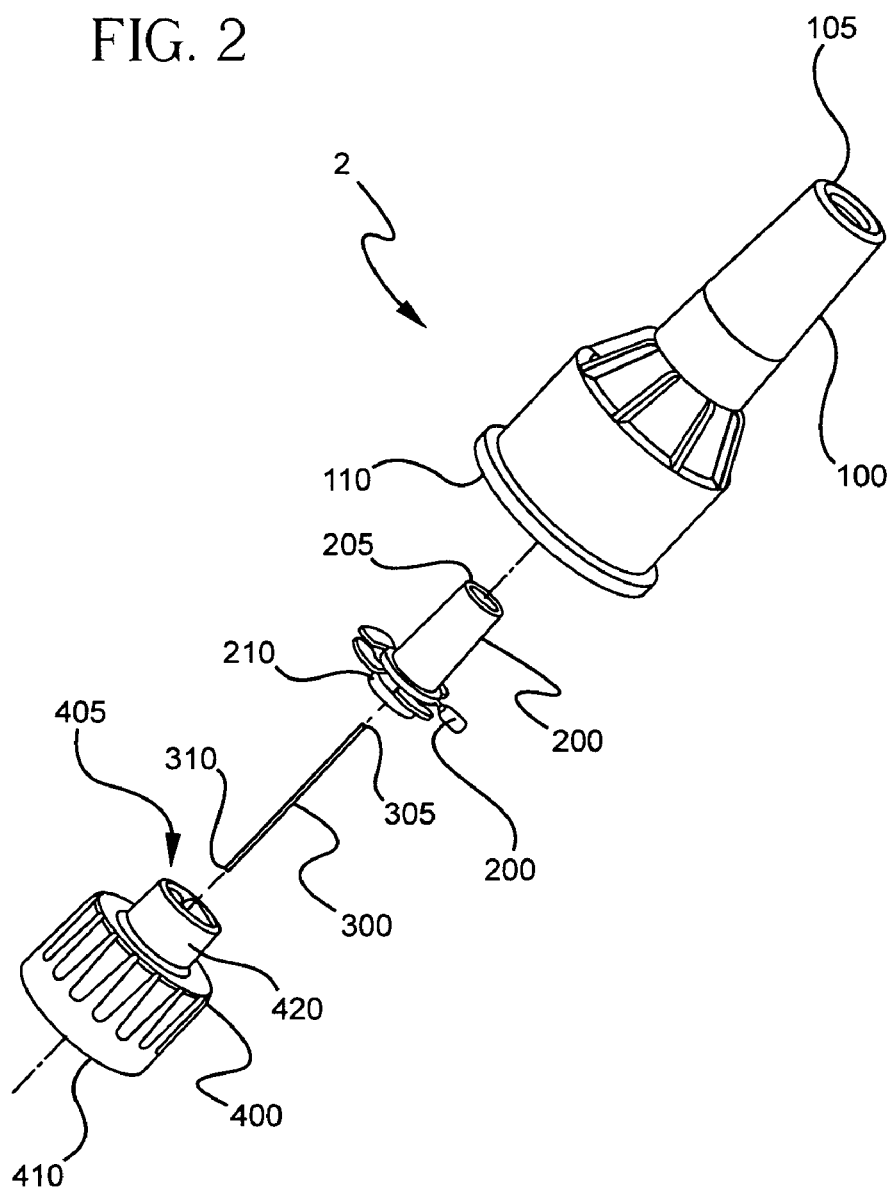
FIG. 2 is an exploded perspective view of a pen needle hub assembly according to an embodiment of the present invention.

A pen needle assembly according to an embodiment of the present invention is shown in FIG. 2. The pen needle assembly 2 comprises a cover 100, an inner shield 200, a needle cannula 300, and a hub 400 The proximal end 310 of the needle cannula 300 is inserted into a center opening in the distal (patient) end 405 of the hub 400 until a predetermined length of the distal end 305 of the needle cannula 300 remains extended. The needle cannula 300 is secured by epoxy or adhesive in the distal end 405 of the hub 400 within the hub protrusion 420.

To protect users from injury and the needle cannula 300 from being damaged, the inner shield 200 covers the exposed portion of needle cannula 300. The open proximal end 210 of the inner shield 200 is placed over the exposed portion of needle cannula 300. The open proximal end 110 of the cover 100 envelops the inner shield 200, needle cannula 300, and hub 400. The cover 100 also pushes down the flexible extensions 220 on the inner shield 200 of this particular embodiment.

Distal end 105 of the cover 100 is closed to prevent contamination and damage to the inner components of pen needle assembly 2, and to prevent injury to anyone who may handle it prior use. The proximal end 410 of the hub 400 is typically covered by a sanitary cover on end 110 of cover 100, which is not shown since it is not an essential element of the instant invention. The pen needle assembly 2 is then ready for shipment to a user. When the user is ready to use the pen needle assembly 2, the sanitary cover (not shown) is removed, the hub 400 is screwed onto a standard pen or medication cartridge (not shown), and the cover 100 and shield 200 are removed from the hub 400/cannula 300 subassembly by a pulling action.

Figure 3:
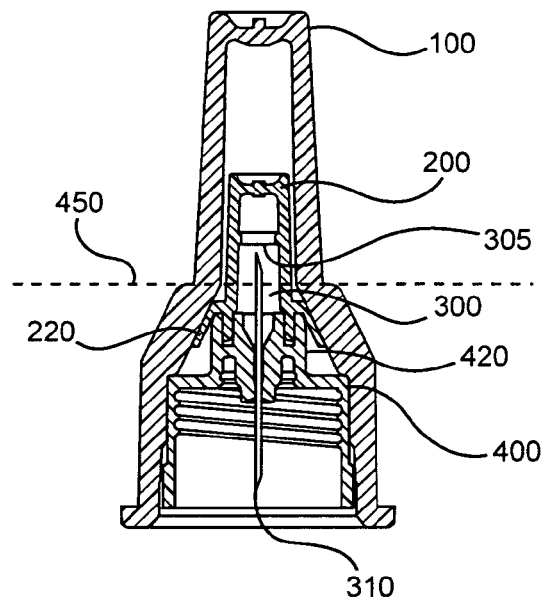
FIG. 3 is a cross-sectional view of the pen needle hub assembly in an as-manufactured state according to an embodiment of the present invention.

FIG. 3 is a cross-sectional view of the pen needle assembly 2 in the configuration that it would be received by a user (with the sanitary cover not shown). The flexible extensions 220 of the inner shield 200 can incorporate a flower petal-shaped or other similar design alignment-assist feature for shielding the proximal or NP end 310 of the needle cannula 300, as described in more detail below. When the pen needle assembly 2 is fully assembled, the flexible extensions 220 will have been intentionally folded over by the cover 100. In addition, the hub 400 comprises center hub protrusion 420. Also shown in FIG. 3 is the skin contact plane 450, which is the plane of the straight surface across the distal end of the center hub protrusion 420. The features of the skin contact plane 450 will be described later in more detail.

Figure 4:
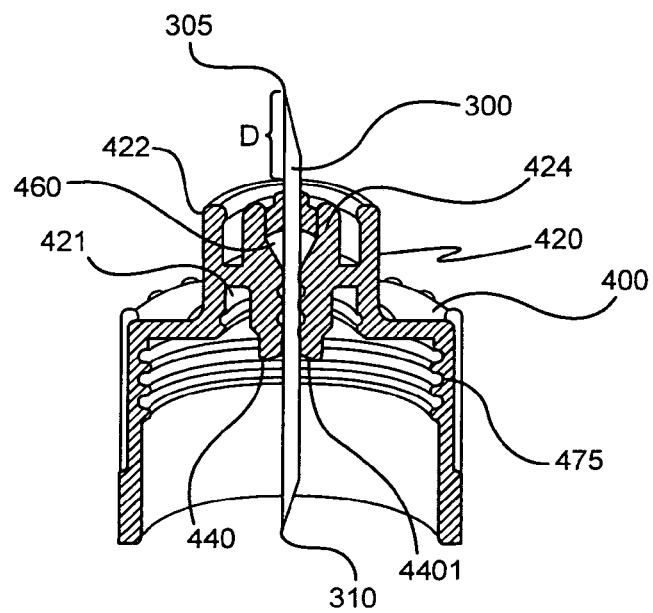
FIG. 4 is a detailed cross-sectional view of the pen needle hub and its center hub protrusion according to an embodiment of the present invention.
Figure 5:
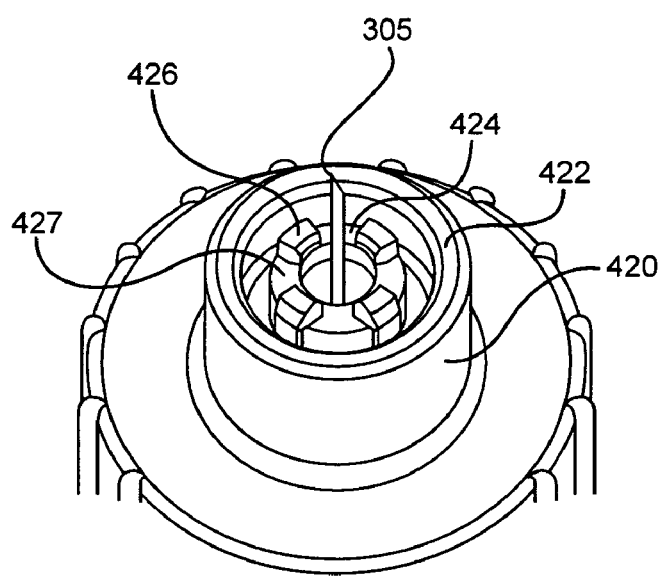
FIG. 5 is a perspective view of the distal end of the center hub protrusion according to an embodiment of the present invention.

A more detailed description of the needle hub 400 will now be provided with reference to FIGS. 4 and 5. The needle hub 400 primarily comprises the center hub protrusion 420, the proximal hub protrusion 440 and screw threads 475. The screw threads 475 are provided to engage a medication cartridge or other suitable medication dispensing device (not shown). A slightly chamfered face 4401 of proximal hub protrusion 440 may be incorporated and serves to direct some compressive forces from the medication cartridge septum (not shown) radially inward to better seal the junction between the outer diameter surface of needle cannula 300 and a medication cartridge septum to reduce the potential for dose loss.

Figure 1:
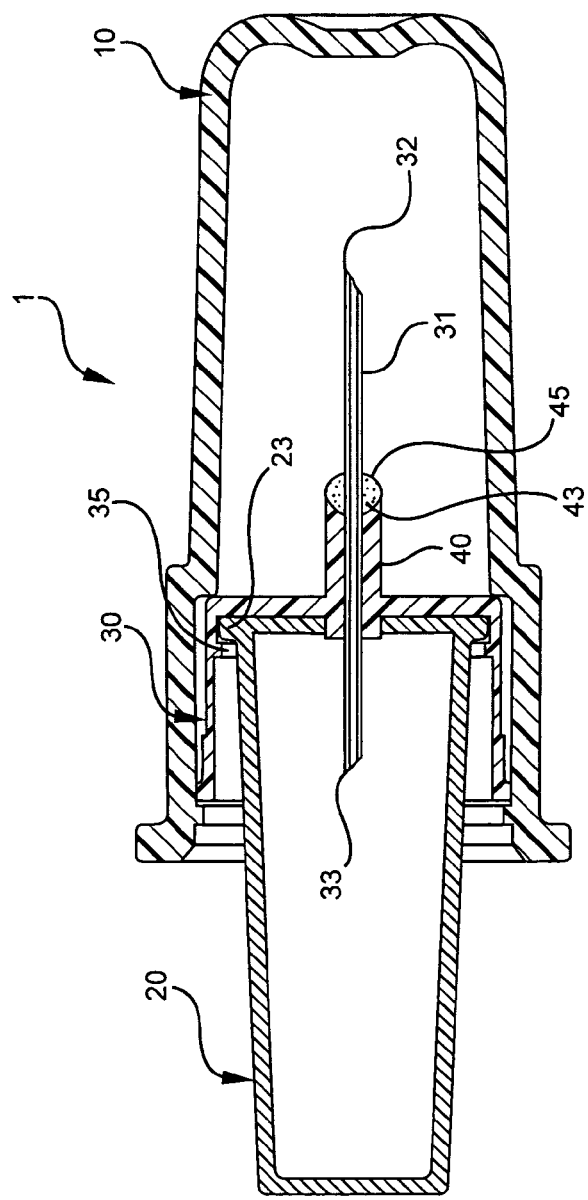
FIG. 1 is an illustration of a needle hub assembly including a cover and a conventional center protrusion, adhesive well and adhesive bump that surrounds the needle cannula.

The one-piece molded part design of the hub 400 allows the effective length of the needle cannula 300 to be limited to length "D", while improving tissue depth targeting accuracy by eliminating the tolerance stack-up potential with multi-component hub assemblies and also affording the ability to be economically manufactured on a mass production scale. The need for targeting accuracy is especially important for shallow subcutaneous and intradermal drug delivery which is described together with the associated length ranges and cannula/bevel design characteristics for narrowing the injection dispersion field, in co-pending patent applications Ser. No. 09/893,746, filed Jun. 29, 2001 and Ser. No. 10/659,245, filed Sep. 10, 2003, both of which are hereby incorporated by reference. Lengths between nearly 0mm to about 12.7 mm can be used, with 3-4 mm being preferred. The epoxy or adhesive well 460 is deeper relative to the skin contact surface plane 450 than it is in the device 1 of FIG. 1.

Figure 19:
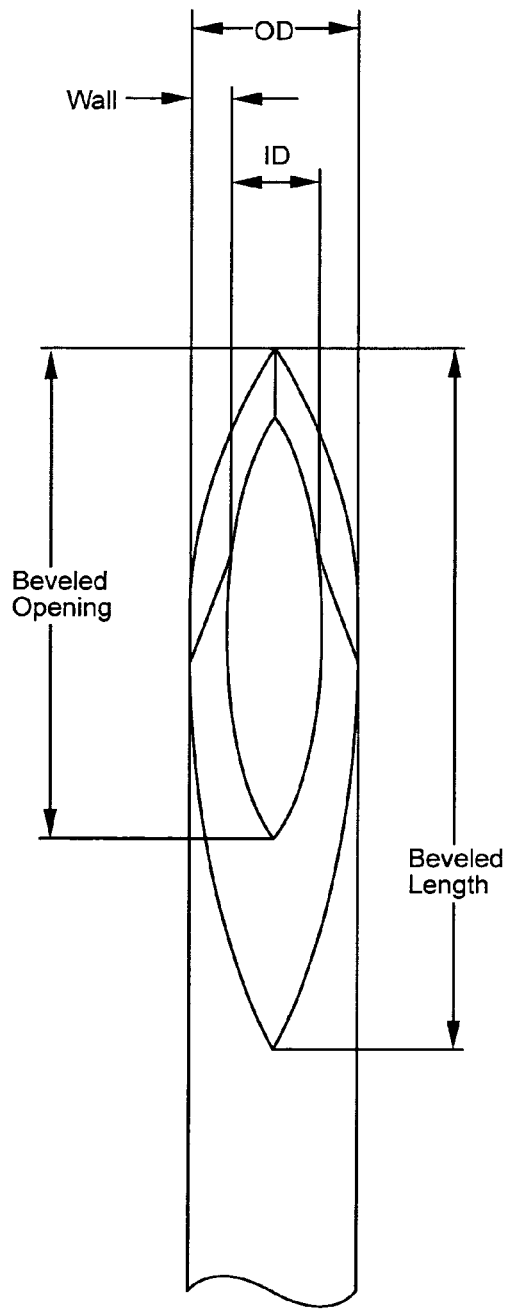
FIGS. 19 and 20 are enlarged views illustrating exemplary cannula designs that are shown not to scale, for use with embodiments of the present invention.
Figure 20:
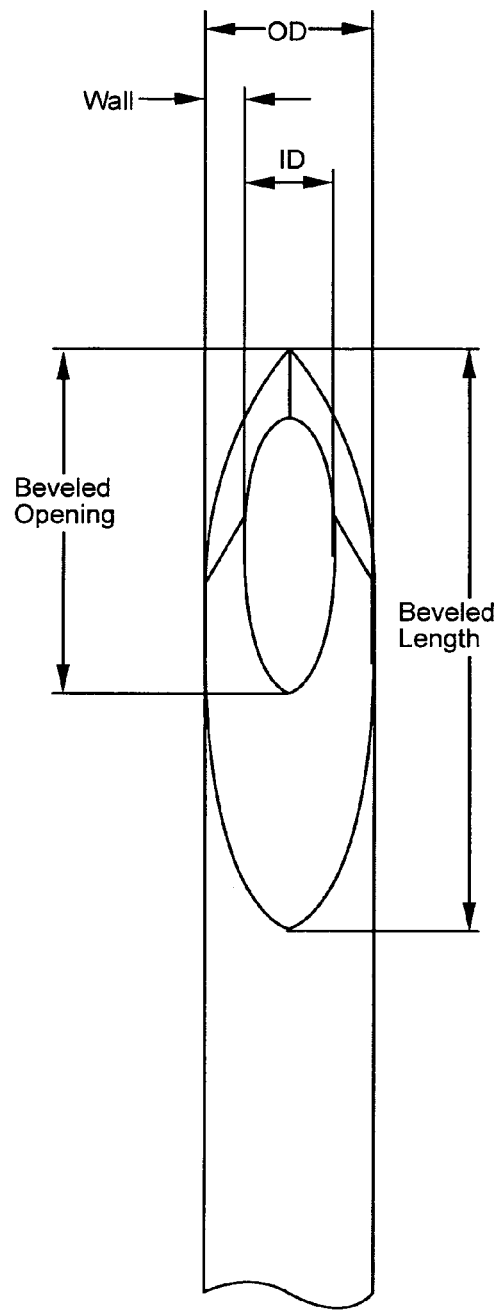
Figure 21:
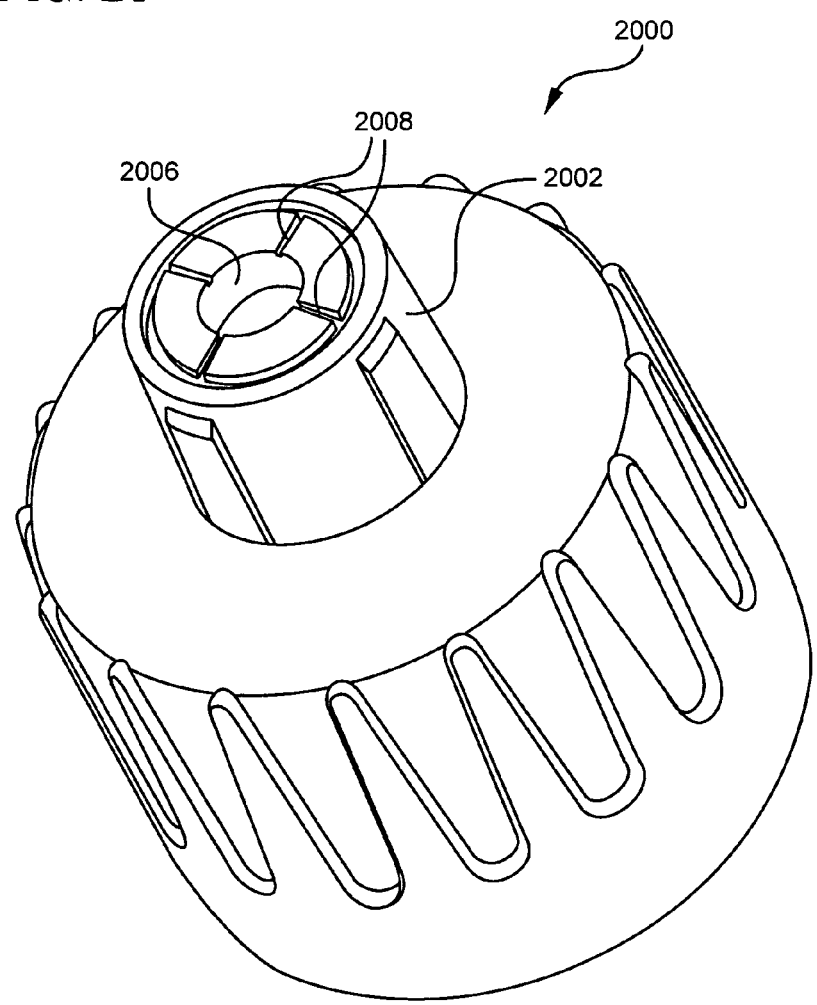
FIGS. 21 through 24 are perspective views of a pen needle hub assembly according to another embodiment of the present invention.
Figure 22:
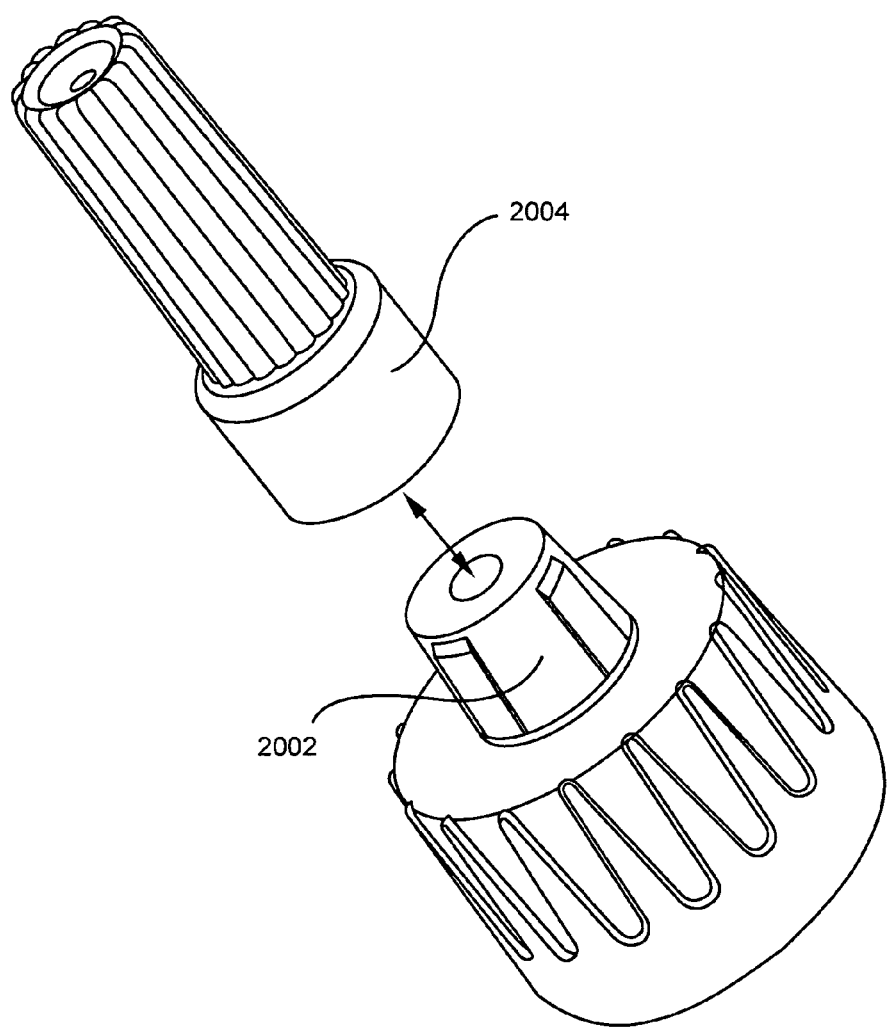
Figure 23:
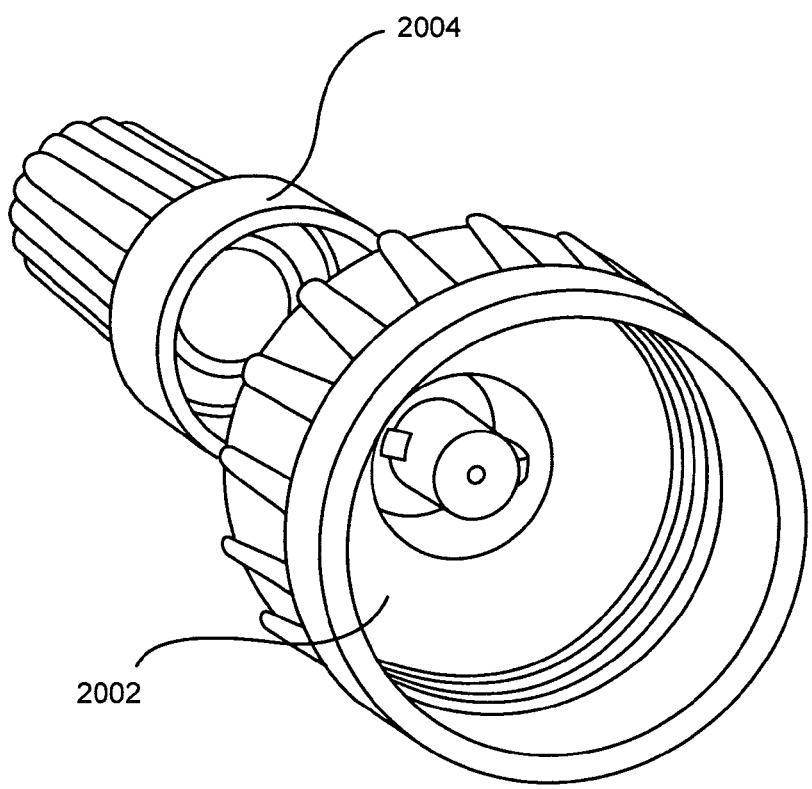
Figure 24:
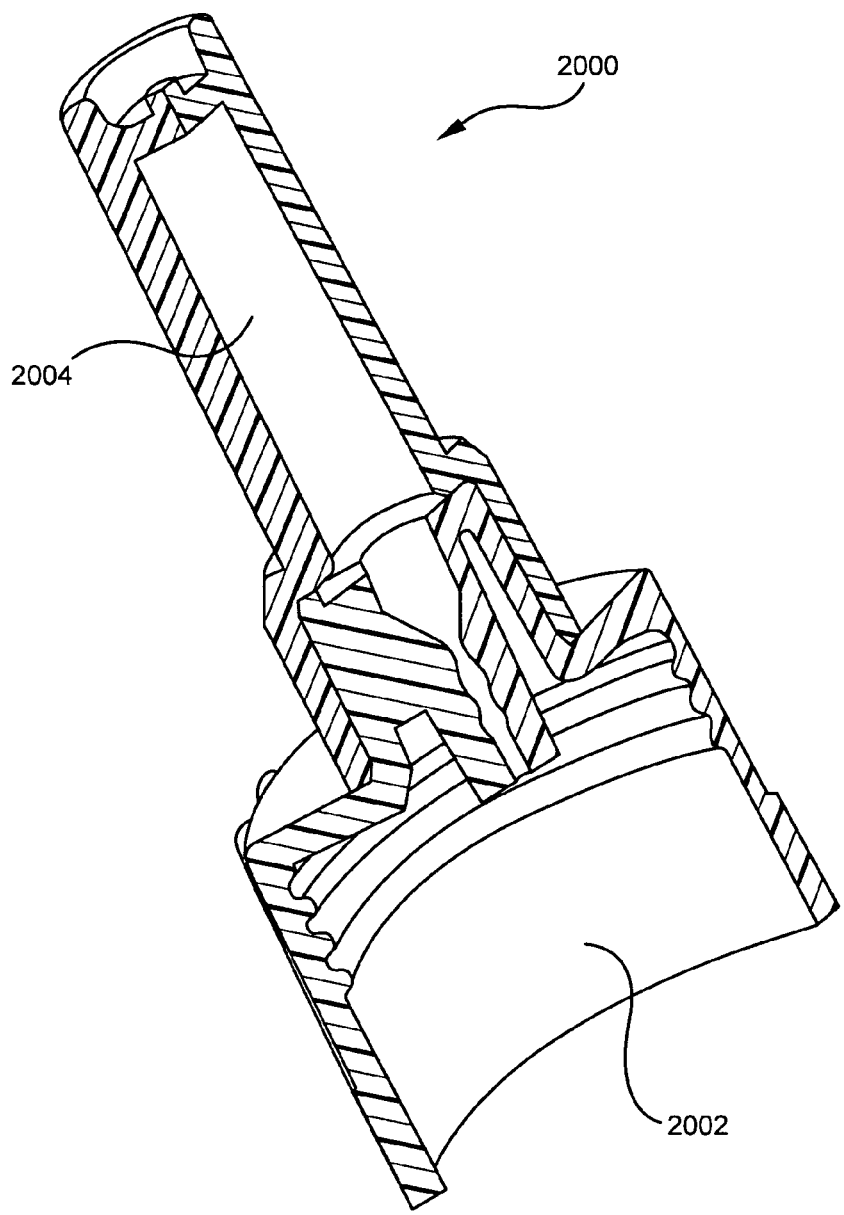

FIGS. 19 and 20 are enlarged views illustrating exemplary cannula designs for use with embodiments of the present invention. The exemplary cannula design characteristics and interactions in FIG. 20 provide an improvement in the injection depth targeting "window" by combining needle length (actual cannula skin piercing "effective length", and needle gauge OD/ID), and point geometry specifics.

FIG. 19 illustrates a standard cannula configuration (for example, one having a longer bevel length point design) according to an embodiment of the present invention, and FIG. 20 illustrates a preferable exemplary cannula configuration (for example, one having a shorter bevel length) according to an embodiment of the present invention for comparison. The point geometry of the configuration of FIG. 19 is less preferable for shallow drug delivery. Accordingly, exemplary point geometry specifications for a 30G standard point of FIG. 19 and an exemplary cannula, such as a 31GTW shortened point embodiment of FIG. 20, that can be used on a 3 mm pen needle, preferably can be provided as in Table 1 below.

TABLE 1

(all dimensions in inches)

| | FIG. 19 30G Standard Point | | FIG. 20 31GTW Shortened Point |
|---|---|---|---|
| OD | 0.0017–0.0126 (preferably about 0.0120) | OD | 0.0010–0.0105 (preferably about 0.01015) |
| ID | 0.0052–0.0070 (preferably about 0.0059) | ID | 0.0049–0.0070 (preferably about 0.0059) |
| Wall | 0.0037–0.00235 (preferably about 0.00305) | Wall | 0.0028–0.0015 (preferably about 0.002125) |
| Bevel Opening | preferably about 0.040 | Bevel Opening | preferably about 0.022 |
| Bevel Length | preferably about 0.057 | Bevel Length | preferably about 0.029 |

The table above shows that for any given effective length for a finished pen needle (which is the distance from the skin contact surface of the hub to the needle point tip), the thinner the gage of cannula used in combination with the shorter bevel (for example, 0.74 mm) point geometry specifications and in combination with the larger ID, deepens the location of the drug delivery relative to the patients' skin with good flow rate characteristics. Obviously, there can be a limit to how far the primary grind angle can be shortened before the point geometry is such that it begins to significantly increase penetration forces which may correlate to increased pain, if it is perceptible. Therefore, in accordance with embodiments of the present invention, to balance these concerns with a need for good needle flow characteristics, a 31GTW cannula tubing is preferably used with the point geometry specification ranges as noted in Table 1, that is, the 31GTW shortened point exemplary embodiment having an OD of about 0.01015 inches, an ID of about 0.0059 inches, and a bevel length of about 0.029 inches, and a having needle effective length (that is, hub to point tip) of about 3 mm.

Returning to FIG. 5, the spaces 427 between the stanchions or castellations 426 on the inner center hub protrusion 424 provide adhesive run-off locations to ensure that no adhesive protrudes above the skin contact plane 450 which can affect the tolerance control over effective length "D" by allowing the adhesive to flow into the space between the inner center hub protrusion 424 and the outer center hub protrusion 422. Alternatively, the stanchions or castellations may be referred to as crenellations or a crenellated feature. The space between the outer center hub protrusion 422 and the inner center hub protrusion 424 retains any adhesive run-off, should it occur, and also provides a pocket between the outer center hub protrusion 422 and the inner center hub protrusion 424 into which the inner shield 200 can be seated and secured by means of an interference or press fit. This results in a larger diameter, depth-limiting skin contact plane 450, which aids in promoting the use of a perpendicular insertion and seating technique with the skin, and full penetration of the needle cannula 300 into the tissue to the targeted depth as intended by the manufacturer.

The effective needle length or depth D (FIG. 4) is measured from the skin contact plane 450 to the distal needle point tip 305. The larger diameter skin contact plane 450 reduces the potential for "pressure point" bruising and the effective needle length variability normally experienced with the smaller diameter dispensed adhesive bump (45 in FIG. 1) typically present to varying degrees beyond the needle hub tip and around the outside of the needle cannula 300. The flat and larger diameter skin contact plane 450 easily provides "positive feedback" to the user that full penetration has been accomplished, reducing the tendency to over-exert insertion/seating force with the smaller diameter center hub protrusion and adhesive bump found in the conventional device which can lead to pain and bruising.

Figure 15:
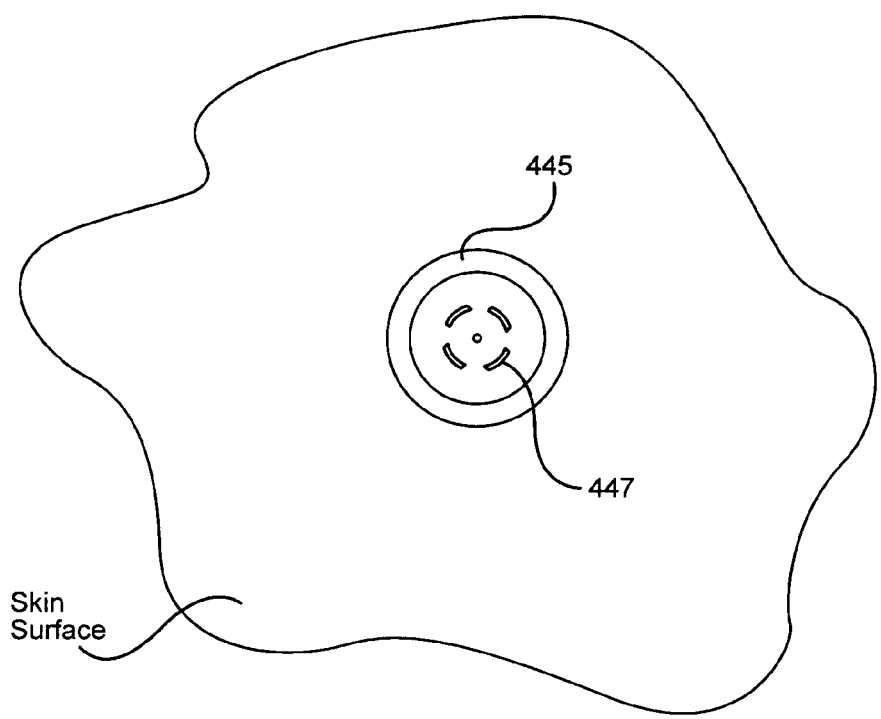
FIG. 15 is a view of a skin surface impression given by the center hub protrusion of FIG. 5.

In an exemplary embodiment of the present invention, the skin contact plane 450 includes the surfaces of the inner hub stanchions or castellations 426 and the surface of the outer center hub protrusion 422, which may be uniform. When the skin contact plane 450 is properly seated with adequate pressure during the course of an injection, a uniquely configured skin impression will typically result as shown in FIG. 15. FIG. 15 is a view of a skin surface impression given by the center hub protrusion of FIG. 5. This skin impression could further serve as a positive reinforcement visual training aid to the user, over time helping the user to better understand and refine his or her injection technique for perpendicularity and positive-pressure skin seating to improve the outcome of each injection. In the exemplary embodiment described herein, a proper injection technique would result in a skin impression having a full circular ring 445 with four dots 447 inside surrounding the needle skin penetration site, all of which have a uniform quality of impression left behind, suggesting a perpendicular approach.

Conversely, if the needle 300 were not inserted completely and the skin contact plane 450 did not positively engage and seat on the skin, either no impression or a very faint impression would be left behind, suggesting that the injection technique should be modified for subsequent injections to ensure that the intended drug delivery depth is reached. Similarly, a half ring impression from the outer center hub protrusion 422 with two or three dots from the inner hub stanchions 426, or a full impression with a ring and four dots having lateral variation in quality of impression, might reflect a non-perpendicular insertion approach, which also suggests that the injection technique should be modified for subsequent injections. Of course, any other generally concentric shape variations, such as rings and cylinders, polygons, individual stanchions or standoffs, and the like, or a single ring and cylinder or other polygon-shaped variation of the inner center hub protrusion 424 or outer center hub protrusion 422 configuration, can be used. Whichever type of hub shape is used, it would preferably allow the ability to receive a needle shield component. Also, one or more deviated planar skin contact surfaces or stanchions 426 can be used.

By eliminating the pronounced adhesive bump typical of conventional pen needle hubs located specifically at the distal tip of the center protrusion 40, the needle cannula 300 is protected from damage due to misuse or inadvertent damage from poor injection technique. The potential failure mode becomes especially critical as needle. cannula 300 sizes and wall thicknesses are made thinner to reduce patient discomfort during injection. As needle cannula 300 lengths and thicknesses are reduced, the needle cannula 300 becomes inherently weaker and unable to withstand misuse and/or deviations from the recommended injection techniques. The exemplary embodiment of the novel hub design has protective features included which serve to address these issues, and may facilitate the ability to incorporate very small gauge (thin), straight needle cannulae which are optimal for patient comfort and also most economically manufactured on a mass-production scale. These features include ergonomics to promote proper perpendicular insertion, a center hub protrusion design with protective benefits for poor technique during both needle insertion and withdrawal, and finally the sunken adhesive well that effectively elongates the needle length from the adhesive to the tip without affecting the effective needle penetration depth "D". When considering this in terms of a cantilever beam problem governed by the following equation (1), $$y_{max} = (P \times L^3)/(3 \times E \times I) \quad (1)$$

wherein y is the tip deflection of the cannula/beam, P is the lateral point force applied at the tip, L is the "exposed" needle length protruding from the adhesive considered rigid, E is the flexural modulus of elasticity, and I is the moment of inertia, and assuming P, E, and I are held constant, the ability to increase length L has an exponential improvement upon maximum deflection y, allowing a more flexible and thus more forgiving cannula to reduce kinking and/or fracture.

Similarly, one could take advantage of the length-enhancing benefits of the design to allow the reduction of cannula diameter and/or wall thicknesses, with a net effect of reducing the moment of inertia (I), which for the same applied force and material characteristics would increase the allowable deflection ($y_{max}$) before reaching a yield condition. As the desire continues for manufacturers to reduce needle gages and lengths aimed at improving patient comfort, the design features of this needle hub better accommodate the ability to accomplish this goal with a straight needle cannula, having optimal drag force characteristics, whereas other manufacturers have had to resort to tapered needle configurations from a strength perspective (see for example, U.S. Pat. No. 6,843, 783 and EP1449555A1).

Figure 6:
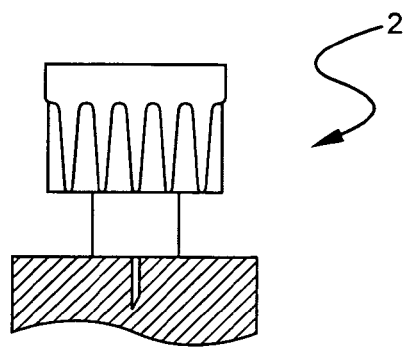
FIG. 6 is a view of the pen needle assembly according to an embodiment of the present invention in the proper, substantially perpendicular position for injecting medication into a patient.

In the illustrated embodiments of the present invention, the first level of protective benefit from the design is that the user is ergonomically led toward a proper, substantially perpendicular insertion technique as a result of the planar skin contact surface 450 substantially perpendicular to the needle cannula 300 that is intended to be fully seated with the skin before injecting (FIG. 6). The second level of protective benefit lies in the design of the center hub protrusion 420 which provides a mechanical advantage aimed at preventing needle cannula 300 damage by eliminating singularly-localized stress concentrations, which allows the needle hub assembly to be more forgiving during misuse or improper use and helps prevent the needle cannula 300 from bending to the point of buckle or fracture. This in-essence provides protective benefit similar to that achieved with conventional strain relief design features typically found in the area of electronic connections.

Figure 7:
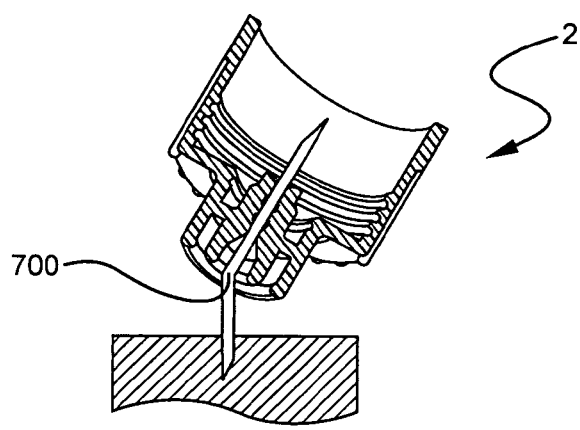
FIG. 7 is a cross-sectional view of the pen needle assembly according to an embodiment of the present invention being subjected to lateral stress.

During the insertion and penetration process, if the needle approach were improperly performed at an extreme angle off of perpendicular, or if the distal tip 305 of the needle cannula 300 were to pierce the skin followed by lateral movement or bending movement applied to the injection device, such as a pen, syringe, or the like, the cannula would first start to bend at the junction of the adhesive and cannula (hereinafter referred to as the adhesive/cannula junction 700) inside the adhesive well pocket as shown in FIG. 7. However, if the user continued with this improper technique, which would result in further needle cannula 300 bending, the needle cannula 300 would come into contact with the inner wall of the adhesive well pocket 460. This would then shift the stress concentrations from the adhesive/cannula junction 700 to the inner wall of the adhesive well 460 or point 702, causing the needle cannula 300 to yield now in a different/secondary location, preventing further bending at the primary adhesive/cannula junction 700 location which could lead to excessive angular displacement and the potential for complete buckling and/or fracture.

Figure 8:
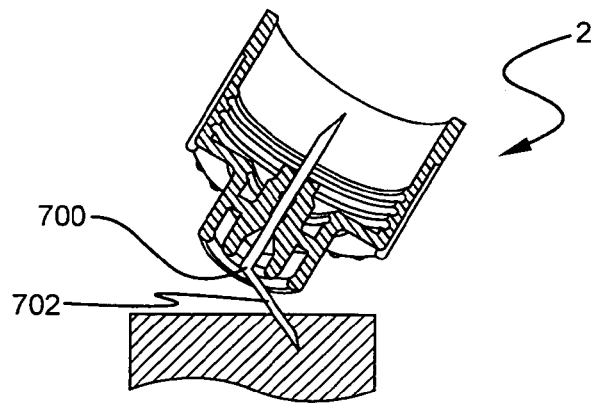
FIG. 8 is a cross-sectional view of the pen needle assembly of FIG. 7 being subjected to severe lateral stress.

In this embodiment, the needle cannula 300 is prevented from exceeding a known maximum angular displacement well below a full 90° as shown in FIG. 8. Prevention of complete buckling and/or fracture through dividing a nearly complete 90° foldover condition over at least two different stress concentration locations, each having a much smaller individual angular bend displacement, helps to minimize the adverse effects resulting from a misuse condition and reduce the chance of a potential needle cannula 300 fracture during the injection process.

Figure 9:
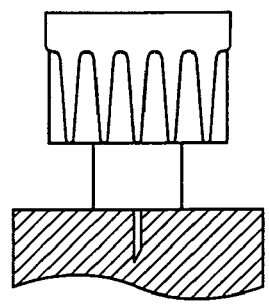
FIG. 9 is a view of a pen needle assembly according to an embodiment of the present invention in the proper, substantially perpendicular position for injecting medication into a patient.
Figure 10:
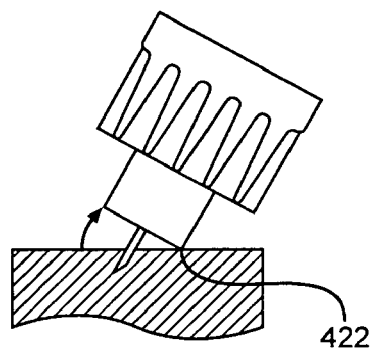
FIG. 10 is a view of the pen needle assembly of FIG. 9 being subjected to angular torque during improper, non-perpendicular withdrawal of the needle after an injection has been performed.

The same would hold true in the case of an applied, purely lateral movement of the injection device, such as a pen, syringe, or the like (not shown), relative to the skin while the needle was either partially or fully seated within the tissue (see FIG. 9). This might occur from improper injection technique either during insertion, during withdrawl, or through inadvertent excessive movement during the delivery of the medicament itself. If, however, through inadvertent angular movement of the injection device during the injection process or removal from the skin post-injection, angular movement of the injection device relative to the skin takes place while the needle cannula 300 is fully seated within the tissue, another feature is invoked as a means of reducing the potential for needle cannula 300 damage or fracture. In this scenario, the outer center hub protrusion 422 acts as a fulcrum, allowing the needle cannula 300 to bend only a given, mathematically calculable, angular displacement before being pried or withdrawn from the tissue should further angular movement of the injection device continue (see FIG. 10).

Figure 11:
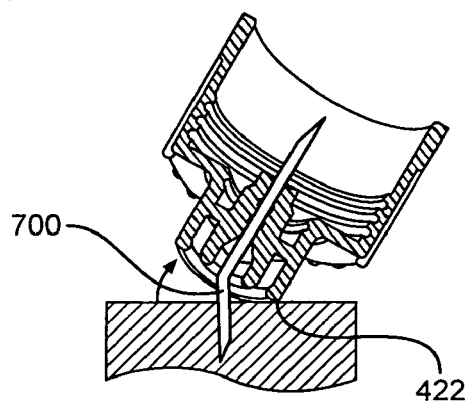
FIG. 11 is a cross-sectional view of the pen needle assembly of FIG. 9 being subjected to additional angular torque.

As similarly stated above, this also serves to shift the localized stress concentrations incrementally toward the distal tip point of needle cannula 300 as the angular displacement of the injection device is incrementally increased from a perpendicular plane relative to the skin. The larger the diameter of the outer center hub protrusion 422, or the distance from the central axis for whatever non-cylindrical fulcrum feature is incorporated, the less the needle cannula 300 can be angularly flexed or bent before initiating the prying and withdrawal process described as the angular displacement of the injection device is incrementally increased (See FIG. 11).

Beyond purely lateral or purely angular movement of the injection device, such as a pen, syringe, or the like (not shown), the only way to further bend the needle cannula 300 would be through additional misuse or poor technique whereby there is a combination of angular movement of the injection device and a lateral or shearing movement. If such a situation occurs multiple times, the damage prevention characteristics of the center hub protrusion 420 explained above help prolong the ability of the needle cannula 300 to withstand ultimate fracture. The damage prevention characteristics inherent to this hub 400 design increase the feasibility of incorporating smaller gauge (31G and higher) straight needle cannulae 300 with thinner wall thicknesses into an acceptable, mass-produceable, consumer product without necessitating costly cannula design enhancements such as full or partial tapering in a compromise effort to balance strength, durability, and user comfort.

Figure 16:
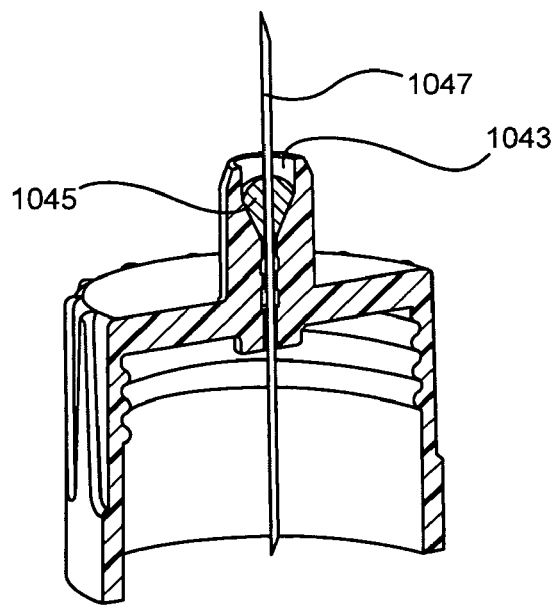
FIGS. 16, 17 and 18 are cross-sectional views of the pen needle hub assembly according to another embodiment of the present invention.
Figure 17:
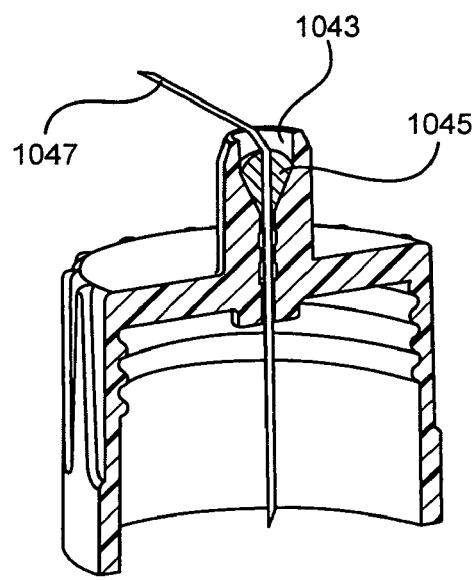
Figure 18:
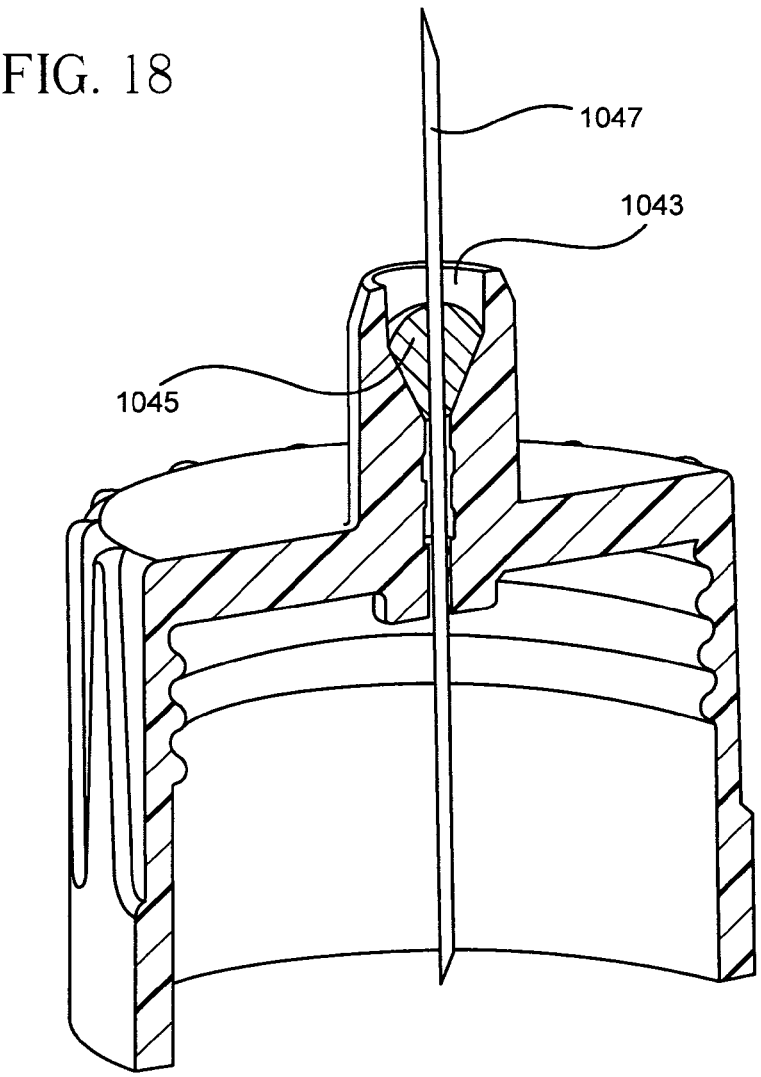

FIGS. 16, 17 and 18 illustrate another embodiment of the present invention in which the same or similar benefits can also be achieved. FIGS. 16, 17 and 18 are cross-sectional views of the pen needle hub assembly according to another embodiment of the present invention. In this exemplary embodiment, the adhesive well 1043 is deepened such that the adhesive bump 1045 is submerged. In doing so, the deepened well/submerged adhesive limits maximum angular bend at the adhesive/cannula joint and creates another at the hub wall tip as shown in FIG. 17. This eliminates the full 90 degree potentially destructive bend into two smaller mechanically tolerable bends. The exemplary embodiment shown in FIGS. 16, 17 and 18 provides for a means of strengthening cannula toughness/durability to withstand severe mishandling/misuse through hub manufacturing improvements, which allows very small, thin standard mass production cannula to be used. This exemplary embodiment provides a strain relief feature (without separate inner and outer hubs), eliminating the need as in conventional devices for costly cannula manufacturing methods, such as fully or partially tapered cannula which can yield sub-optimal patient comfort characteristics.

Figure 12:
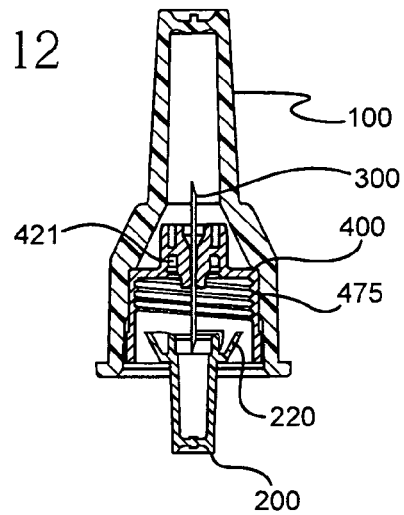
FIGS. 12, 13 and 14 are sequence views illustrating the placement of the inner shield over the proximal end of the needle cannula and within the proximal end inner shield receiver according to an embodiment of the present invention.

FIG. 12 illustrates the insertion of the inner shield 200 into the non-patient (NP) or proximal end 410 of the hub 400. After an injection is administered, the needle cannula 300 and the hub 400 attached to the pen injection or similar device (not shown) is lowered into the upturned cover 100, without the inner shield 200, for safe recovery using one-handed technique. Alternatively, the cover 100 can be held in one hand with the needle cannula 300 and the hub 400 mounted onto the pen injection or similar device (not shown) in the other hand, and the two press-fit back together to recover the needle cannula 300 for storage and disposal.

As noted earlier, the inner shield 200 can incorporate a flexible extension 220 aimed at helping the consumer, especially those with impaired visibility and dexterity, to align the shield 200 and covered needle 300 when shielding the NP or proximal end 310 of the needle cannula 300. Upon removal of the shield 200 from the needle hub assembly 2 prior to injection, the shield's 200 flexible extensions 220 are in a folded-over condition from the hub 400 being mounted with the shield 200 into the cover 100 at the time of manufacture. The shield 200 is then placed on a flat surface, upside down in this situation, in preparation for shielding the proximal needle cannula point 310 after injection using proper needle stick prevention technique. The flexible extensions 220 in the folded-over condition extend beyond the plane comprising the open end 210 of the shield 200, such that when the cover 100 and the needle hub assembly 2 are lowered onto the shield 200, the flexible extensions 220 first encounter and fit within the entry diameter of the outer cover 100, followed by the entry diameter of the hub 400.

Figure 13:
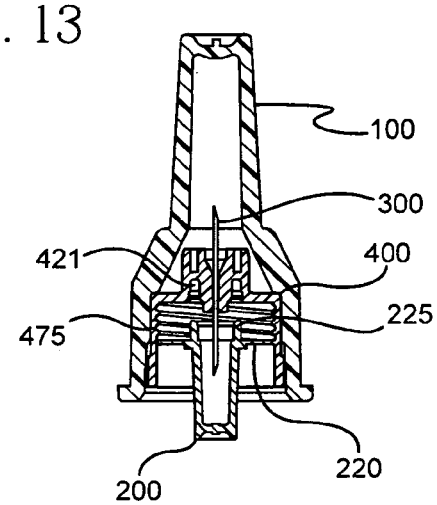
Figure 14:
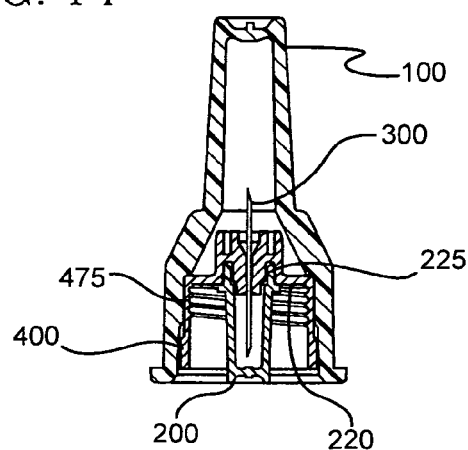

As the shield 200 is aligned, the entry plane of the shield 200 reaches the NP or proximal end 310 of the needle cannula 300 tip, ensuring that the shield 200 will freely slide over and cover the proximal end 310 of the needle cannula 300 and with continued lowering of the cover 100 and the needle cannula 300 over the shield 200 (see FIG. 12). As the cover 100 and the needle cannula 300 are lowered further, the diametric span of the flexible extensions 220 can be designed to come in contact with the hub threads 475. Continued lowering of the cover 100 and needle 300 onto the shield 200 will result in the flexible extensions 220 first straightening (FIG. 13) and perhaps even folding over in the opposite direction as the cover 100, needle 300 and shield 200 are snapped into place (FIG. 14). In this case, the flexible extensions 220 can serve to further hold the shield into place, thereby raising the force necessary to un-snap the shield if such were attempted. The shield 200 is prevented from lowering further by the bottom of shield flange seating onto the inner roof surface of hub 400. The overall length of the needle shield is preferably such that if the NP-shielding feature is used the end of the shield falls approximately at or below the entry plane of the cover 100 and hub 400, making it very difficult to catch on something and be pried off inadvertently or to allow fingers to grasp the tip of the needle shield in an attempt to remove it from its final snap-locked position.

With the back end 110 of the cover 100 open such that the non-patient point 310 of the needle cannula 300 is exposed there is the chance of inadvertently being stuck by the needle cannula 300, especially when storing and transporting the needle cannula 300 for subsequent disposal. Additionally, there is a risk of inadvertent needle sticks to others (such as trash handlers, maids, and the like) should the covered needle 300 with an exposed NP end 310 be improperly disposed of in a standard trash container rather than using proper sharps-disposal methods. While the NP end 310 most likely has not been biologically contaminated by the person using the needle cannula 300, this presents at least a potential for injuring the user and/or innocent bystander.

In yet another embodiment of the present invention, a hub design can be provided with the cannula-protective benefits of a deeper well along with an adhesive run-off feature, without having to have inner/outer center hub protrusions and a shield mounted between. FIGS. 21 through 24 are perspective views of a pen needle hub assembly according to another embodiment of the present invention. In the embodiment of FIGS. 21 through 24, the hub 2000 comprises a hub protrusion 2002 and a shield 2004. The embodiment provides a deeper well 2006 along with an adhesive run-off feature via opening 2008. The coring can be done from the bottom side and with the hub protrusion diameter reduced, the shield can mount over the hub protrusion.

Figure 25A:
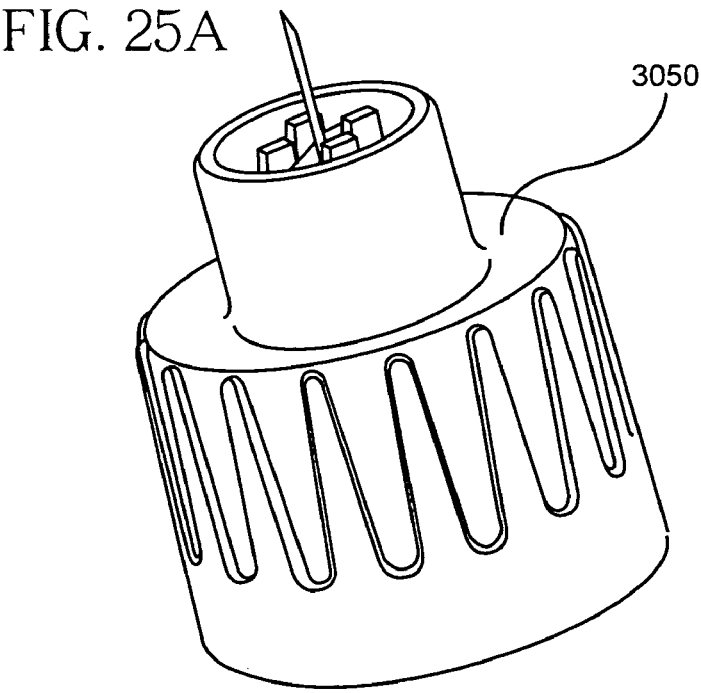
FIG. 25A and FIG. 25B are perspective side-by-side views of a conventional pen needle and another embodiment of the present invention for comparison.
Figure 25B:
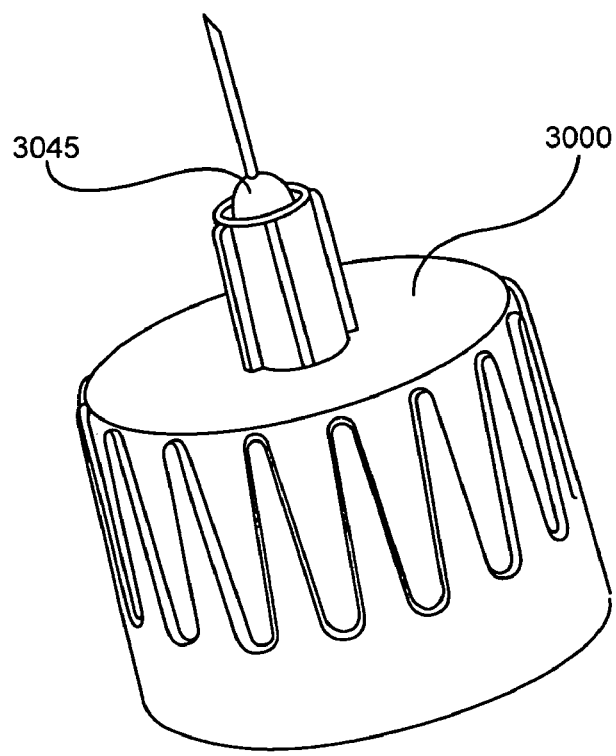
Figure 26:
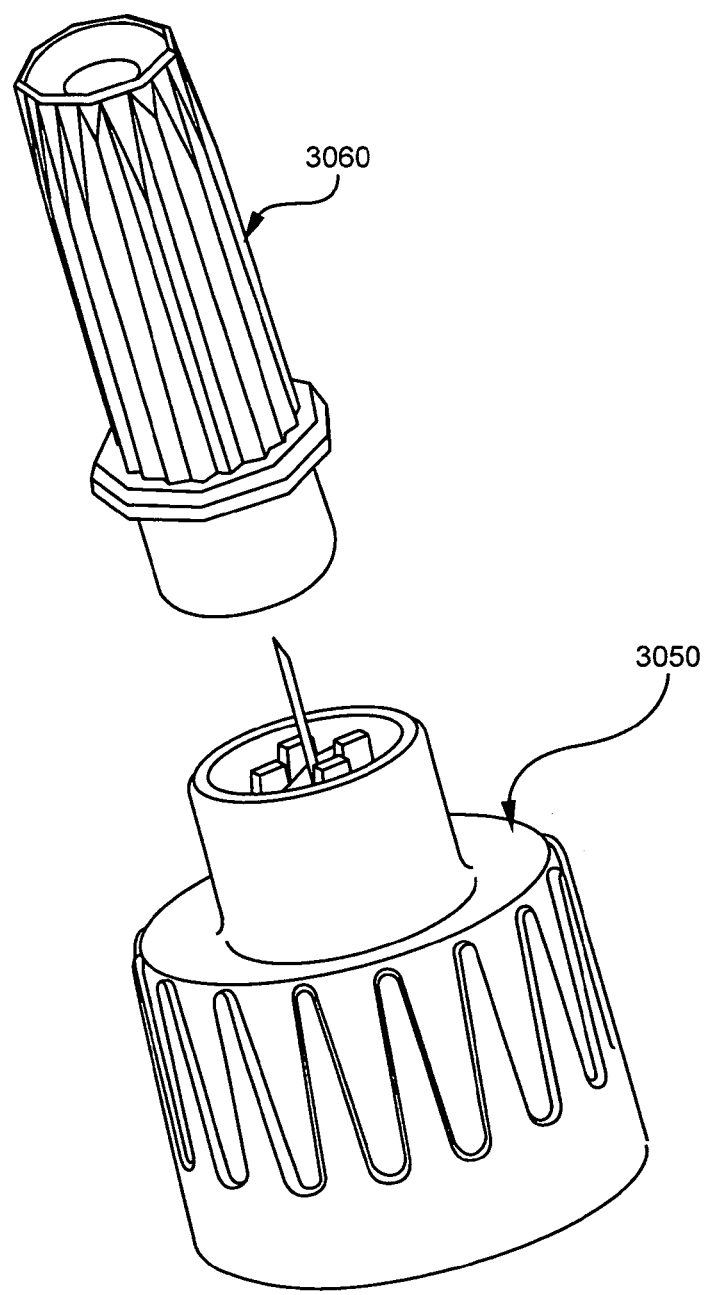
FIG. 26 is a perspective view of the pen needle hub assembly of FIG. 25A and FIG. 25B and shield according to an embodiment of the present invention.
Figure 27A:
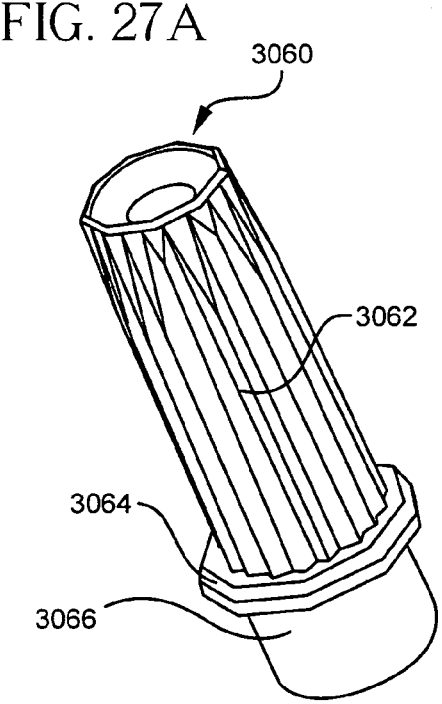
FIGS. 27A though 27D, 28 and 29 illustrate an exemplary embodiment of the shield of FIG. 26.
Figure 27B:
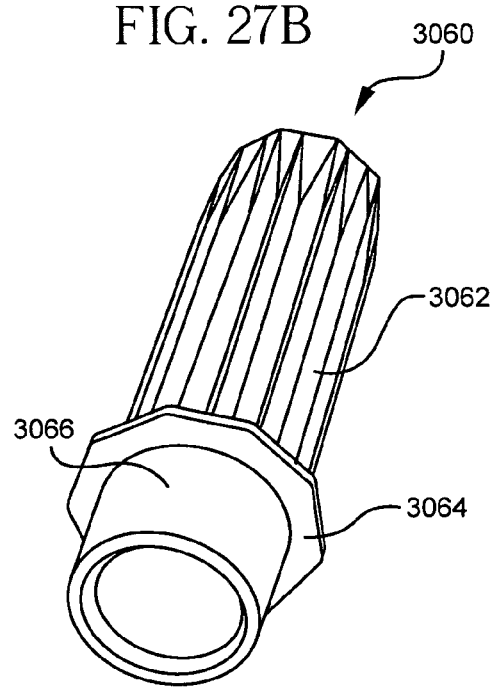
Figure 27C:
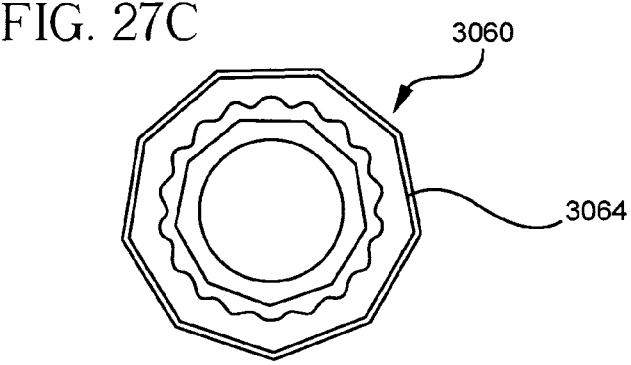
Figure 27D:
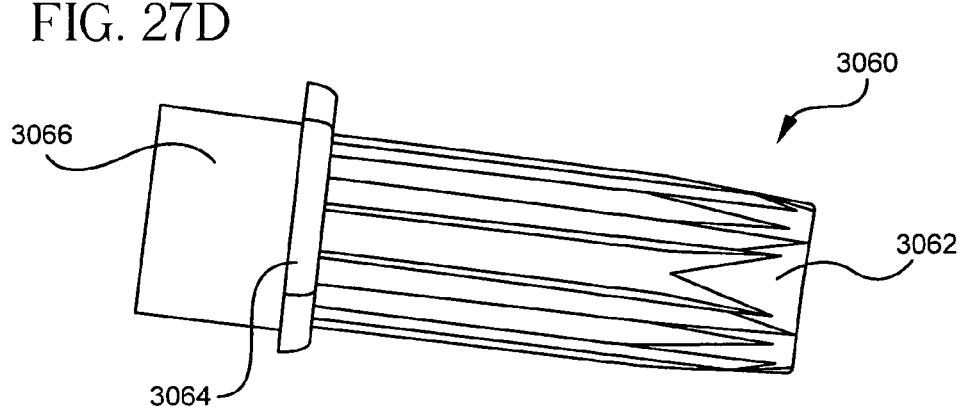

In yet another embodiment of the present invention, the above features can be combined in any number of arrangements. FIGS. 25A through 30 are perspective views of a pen needle hub assembly according to another embodiment of the present invention. Specifically, FIG. 25A and FIG. 25B illustrate a side-by-side comparison between a conventional hub device 3000 and an exemplary embodiment 3050 of the present invention in which a number of features described above have been provided. As can be noted from FIG. 25A, the adhesive bump 3045 of the conventional hub device 3000 of FIG. 25B is not detectable in the exemplary embodiment 3050. Further, as shown in FIG. 26, the exemplary embodiment 3050 can be further provided with a shield 3060. FIG. 26 illustrates an embodiment of the present invention wherein a shield 3060 is shown in a removed state. FIGS. 27A through 27D, 28 and 29 illustrate an exemplary embodiment of the shield 3060.

The shield 3060 of FIGS. 27A through 27D, 28 and 29 is shown having a serrated upper cylindrical body 3062 and a multi-sided shoulder 3064 having a plurality of flat surfaces.

Figure 28:
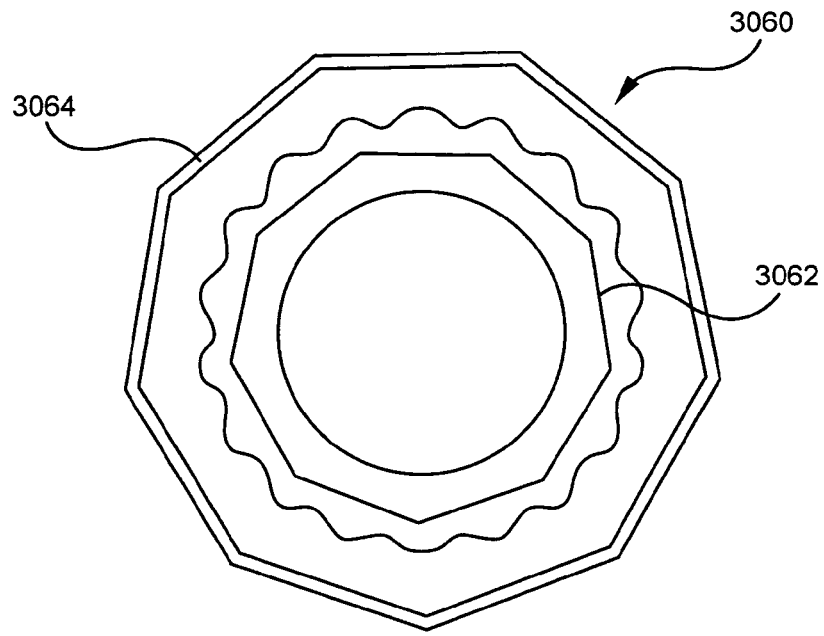
Figure 29:
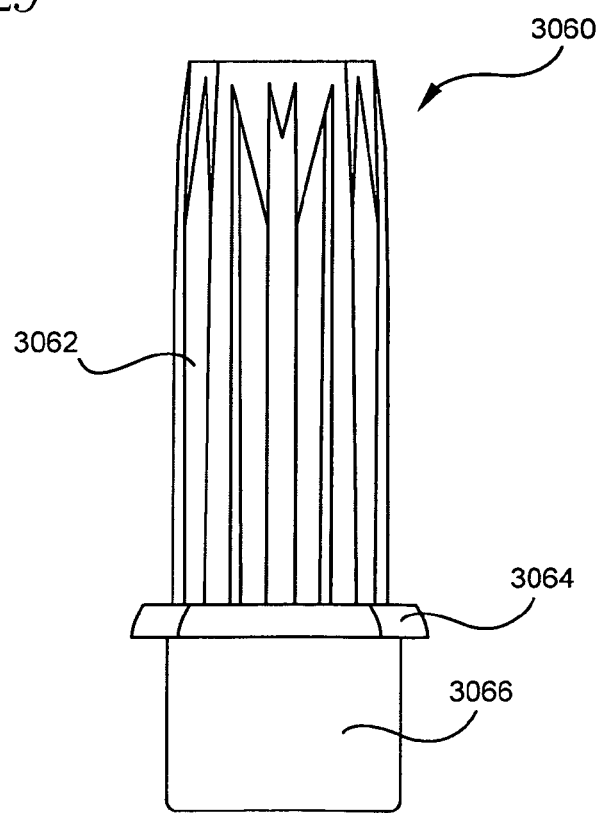

As shown in an exemplary embodiment in FIG. 28, the multi-sided shoulder 3064 can be provided with nine flat surfaces, but is not limited thereto. Any number of flat surfaces can be provided to substantially prevent the device from rolling when placed horizontally upon a surface. In the exemplary embodiment shown in FIG. 28, the nine flat surfaces (or any uneven number of flat surfaces) can also be used to provide maximal land area for the part when traveling along automated assembly feeder rails (not shown). Further, the uneven number of flat surfaces prevents two flat surfaces from being formed directly across from each other, which would minimize the 180 degree span and minimize the land area for engaging automated assembly feeder rails. The elongated upper body 3062 provides further distance between a user and the needle point when assembling the shield with the hub (not shown). A lower body 3066 is provided having an opening for receiving the hub.

Figure 30A:
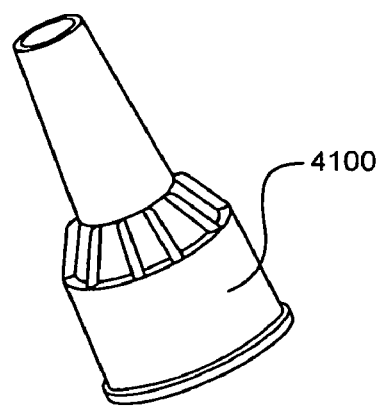
FIGS. 30A through 30F are perspective views of a pen needle hub full assembly according to an embodiment of the present invention.
Figure 30B:
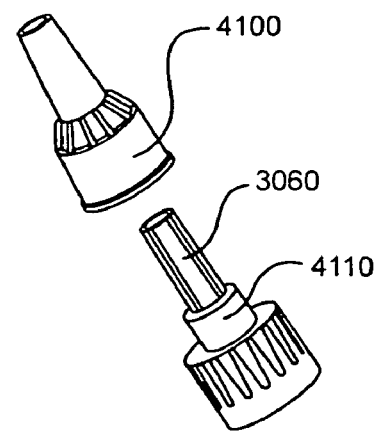
Figure 30C:
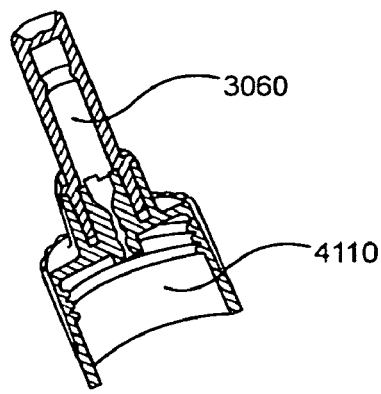
Figure 30D:
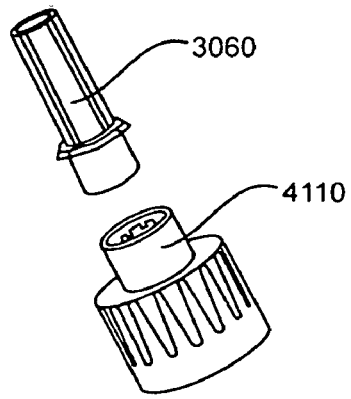
Figure 30E:
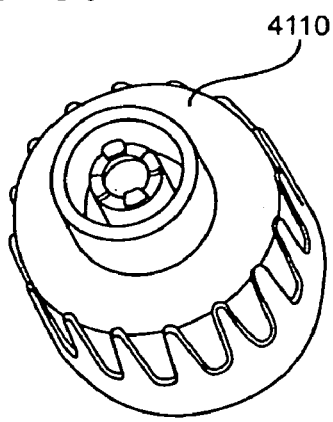
Figure 30F:
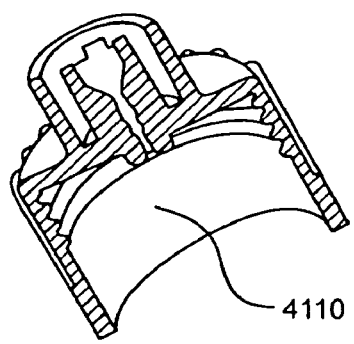

FIGS. 30A through 30F are perspective views of a pen needle hub full assembly, including cover, shield and hub, according to an embodiment of the present invention. FIG. 30A illustrates an exemplary cover 4100, and FIG. 30B illustrates the cover 4100 positioned to cover the shield 3060 already in place upon a hub 4110. FIG. 30C is a cross-sectional view of the shield 3060 in place upon the hub 4110, and FIG. 30D is a view showing the shield 3060 removed from the hub 4110. The hub 4110 is shown in greater detail in FIGS. 30E and 30F, and comprises features described in greater detail above. In the embodiment shown in FIGS. 30A through 30F, the NP shield is not required and all center hub protrusion coring is done from the top. The shield sleeve is longer, providing more engagement with the hub for a more secure fit and is provided with a finger grip surface with full radial serration.

The foregoing embodiments and advantages are merely exemplary and are not to be construed as limiting the scope of the present invention. The description of an exemplary embodiment of the present invention is intended to be illustrative, and not to limit the scope of the present invention. Various modifications, alternatives and variations will be apparent to those of ordinary skill in the art, and are intended to fall within the scope of the invention.

The invention claimed is:

1. An injection needle for use in injecting a substance from a reservoir, comprising:
   a hub having,
      a distal end with a first protrusion having a skin engaging surface defined distally thereon,
      an axial void in said hub having a channel defined at said distal end of said hub and extending through the hub, proximally away from said skin engaging surface,
      a second protrusion having a distal face disposed on said hub substantially encircling said first protrusion, wherein the distal face of the protrusion is positioned co-planar or distal to the skin engaging surface,
      a needle cannula having a sharpened distal end and a proximal end, said needle cannula being secured in said channel with said proximal end being in fluid communication with said reservoir and said distal end of said needle cannula extending from said skin engaging surface a pre-determined distance,
      wherein said skin engaging surface limits penetration of said distal end of said needle cannula to a pre-determined layer of the skin of a patient, and
      a third protrusion having a substantially concave proximal end and from which the proximal end of the needle cannula emerges.

2. The injection needle in claim 1 further comprising a needle shield which is slidably disposed upon said first or second protrusions.

3. The injection needle in claim 2 further comprising a needle shield slidably disposed upon said first protrusion.

4. The injection needle in claim 1 further comprising the hub having an open proximal end for receiving a medication delivery device.

5. The injection needle in claim 1 wherein the skin engaging surface is defined by the distal faces of a crenellated section of the first protrusion and said first protrusion has at least one radial void formed between the crenellated sections.

6. The injection needle in claim 5 wherein the crenellated section of the first protrusion forms a penetration indicator, thereby indicating a full penetration has occurred after the needle has been inserted into a patient's skin, the crenellated section leaves a residual visible mark in the skin.

7. The injection needle of claim 4 wherein the needle cannula has a sharpened proximal end for insertion into a cartridge within said medication delivery device.

8. The injection needle of claim 7 wherein the third protrusion is disposed within said open proximal end of the hub.

9. An injection needle for use in injecting a substance from a reservoir, comprising:
a hub having,
a distal end with a crenellated first protrusion as a skin engaging surface, wherein the skin engaging surface is defined by distal faces of the crenellated sections and said first protrusion has at least one radial void,
an axial void in said hub having a channel defined at said distal end of said hub and extending through the hub, proximally away from said skin engaging surface, wherein said at least one radial void is in fluid communication with the channel and said channel has a predefined volume,
a needle cannula having a sharpened distal end and a proximal end, said needle cannula positioned in said channel with said proximal end being in fluid communication with said reservoir and said distal end of said needle cannula extending from said skin engaging surface a pre-determined distance, wherein said skin engaging surface limits penetration of said distal end of said needle cannula to a pre-determined layer of the skin of a patient, and
an adhesive which secures the cannula in the channel by the filling the volume of the channel, wherein a volume of the adhesive is greater than the volume of the channel, such that an excess amount of the adhesive exits the channel through the at least one radial void, thereby keeping the skin engaging surface substantially free from adhesive.

10. The injection needle in claim 9 wherein the crenellated section of the first protrusion forms a penetration indicator, thereby indicating a full penetration has occurred after the needle has been inserted into a patient's skin, the crenellated section leaves a residual visible mark in the skin.

11. The injection needle in claim 9 further comprising a needle shield which is slidably disposed upon said first or second protrusions.

12. The injection needle in claim 9 further comprising a second protrusion having a distal face disposed on said hub substantially encircling said first protrusion, wherein the distal face of the protrusion is positioned co-planar or distal to the skin engaging surface.

13. The injection needle in claim 12 further comprising the hub having an open proximal end for receiving a medication delivery device.

14. The injection needle of claim 13 wherein the needle cannula has a sharpened proximal end for insertion into a cartridge.

15. The injection needle of claim 14 wherein the hub has a third protrusion having a substantially concave proximal end, the third protrusion disposed within said open proximal end of the hub and from which the sharpened proximal end of the needle cannula emerges.

16. A method of making an injection needle, comprising:
providing a hub having a distal end with a crenellated first protrusion as a skin engaging surface, wherein the skin engaging surface is defined by distal faces of the crenellated first protrusion and said crenellated first protrusion has at least one radial void, and a channel defined at said distal end of said hub and extending through the hub, proximally away from said skin engaging surface, wherein said at least one radial void is in fluid communication with said channel and said channel has a predefined volume,
inserting a needle cannula having a sharpened distal end and a proximal end into said channel,
positioning said needle cannula such that said distal end of said needle cannula extends from said skin engaging surface a pre-determined distance,
applying an adhesive which secures the cannula in the channel by filling the volume of the channel, wherein a volume of the adhesive is greater than the volume of the channel,
allowing an excess amount of the adhesive to exit the channel through the at least one radial void, thereby keeping the skin engaging surface substantially free from adhesive, and
curing the adhesive.

17. The method in claim 16 wherein the adhesive is a light-curable adhesive and the curing step further comprises applying light to the adhesive.

18. The method in claim 16 wherein the steps are performed in the order recited.

19. The method in claim 16 wherein the adhesive is applied to a surface of the cannula prior to insertion.

20. The method in claim 16 wherein the adhesive is applied to the channel.

* * * * *